United States Patent [19]

Platz

[11] Patent Number: 5,369,215

[45] Date of Patent: * Nov. 29, 1994

[54] DEPOLYMERIZATION METHOD FOR RESOURCE RECOVERY FROM POLYMERIC WASTES

[75] Inventor: Gerald A. Platz, Conroe, Tex.

[73] Assignee: S-P Reclamation, Inc., Houston, Tex.

[*] Notice: The portion of the term of this patent subsequent to Nov. 23, 2010 has been disclaimed.

[21] Appl. No.: 107,281

[22] Filed: Aug. 16, 1993

Related U.S. Application Data

[63] Continuation-in-part of Ser. No. 864,426, Apr. 6, 1992, Pat. No. 5,264,640.

[51] Int. Cl.$^5$ .......................... C07C 4/04; C07C 4/06
[52] U.S. Cl. .................................. 585/241; 201/2.5; 241/DIG. 37; 264/37; 264/349; 264/83; 264/DIG. 69; 264/233; 425/DIG. 44
[58] Field of Search .................... 585/241; 264/37, 83, 264/238, 349, 233, 28, 130, DIG. 69; 201/2.5; 241/DIG. 37; 425/DIG. 44

[56] References Cited

U.S. PATENT DOCUMENTS

| | | |
|---|---|---|
| 3,424,822 | 1/1969 | Liston . |
| 3,494,958 | 2/1970 | Mannsfeld et al. . |
| 3,558,589 | 1/1971 | Bethea et al. . |
| 3,582,279 | 5/1971 | Beckman et al. . |
| 3,704,108 | 11/1972 | Alpert ....................... 44/62 |
| 3,974,206 | 8/1976 | Tatsumi et al. . |
| 3,978,199 | 8/1976 | Maruhnic et al. ............. 423/461 |
| 3,996,022 | 12/1976 | Larsen ....................... 44/1 |
| 3,997,407 | 12/1976 | Fujii et al. .................. 202/221 |
| 4,025,990 | 5/1977 | Lovette, Jr. .................. 241/14 |

(List continued on next page.)

FOREIGN PATENT DOCUMENTS 47-3017  8/1972  Japan .

OTHER PUBLICATIONS

"Pyrolysis of Polymers", Chapter 6, by Walter Kaminsky, 1992, pp. 60-72.
"Thermocatalytic Degradation of Butyl Rubber in Presence of Combinations of AICl$_3$ With Some Metal Chlorides", S. R. Ivanova et al., Polymer Science U.S.S.R., pp. 265-272 (1983).
"Scrap Tires: A Resource and Technology Evaluation of Tire Pyrolysis and Other Selected Alternate Technologies," J. Dodds et al., prepared for the U.S. Department of Energy and Idaho National Engineering Laboratory, DE-AC07-761D01570, Nov. 1983.
"Waste Tire Utilization," R. L. Hershey et al., prepared for the U.S. Department of Energy, Office of Industrial Programs, AC01-84CE40714, Apr. 30, 1987.
"Raw Material Recovery From Scrap Tires and Plastic Waste by Pyrolysis," W. Kaminsky et al., pp. 681-685.
"Recycling of Scrap Rubber as a Filler for Thermoplas-

(List continued on next page.)

Primary Examiner—Mathieu Vargot
Attorney, Agent, or Firm—Arnold, White & Durkee

[57] ABSTRACT

Polymeric feedstocks, such as scrap or waste tires, rubber, and plastics, in a size range of −6 to +25 mesh are washed with an organic solvent to remove stabilizing additives which have migrated to the surface of the polymer particles, thus eliminating the stabilizers from participation in subsequent reactions and allowing the final production of more pure monomeric products. The polymer particles are exposed to ozone under conditions to cause stress cracking, fissuring and cleavage of the polymer feedstock particles. The ozonated polymer particles are depolymerized to produce one or more monomeric compounds, with the reaction taking place rapidly and occurring in the presence of a system of one or more catalysts which may be metallic salts. The depolymerization is accomplished under conditions of elevated temperatures and reduced pressure, the conditions being less severe than those conditions associated with thermal pyrolysis. The monomeric compounds are recovered by conventional means from otherwise waste polymers and are recycled. Other products of this invention may be collected and recycled or disposed of with no adverse impact on the environment.

15 Claims, 3 Drawing Sheets

U.S. PATENT DOCUMENTS

| | | | |
|---|---|---|---|
| 4,029,550 | 6/1977 | Mitsui et al. | 201/2.5 |
| 4,030,984 | 6/1977 | Chambers | 201/25 |
| 4,045,370 | 8/1977 | Cares | 252/458 |
| 4,051,212 | 9/1977 | Grigat et al. | 264/102 |
| 4,082,615 | 4/1978 | Komuro et al. | 201/12 |
| 4,098,649 | 7/1978 | Redker | 201/2.5 |
| 4,108,730 | 8/1978 | Chen et al. | 201/2.5 |
| 4,175,211 | 11/1979 | Chen et al. | 585/241 |
| 4,240,587 | 12/1980 | Letsch | 241/23 |
| 4,250,158 | 2/1981 | Solbakken et al. | 423/449 |
| 4,284,616 | 8/1981 | Solbakken et al. | 423/461 |
| 4,402,791 | 9/1983 | Brewer | 585/241 |
| 4,426,459 | 1/1984 | Watabe et al. | 585/241 |
| 4,430,160 | 2/1984 | DuBow | 201/19 |
| 4,452,154 | 6/1984 | Kono et al. | 110/346 |
| 4,452,155 | 6/1984 | Ishihara et al. | 110/346 |
| 4,458,095 | 7/1984 | Wingfield, Jr. et al. | 585/241 |
| 4,507,174 | 3/1985 | Kutrieb | 585/241 |
| 4,515,659 | 5/1985 | Wingfield, Jr. et al. | 201/2.5 |
| 4,577,564 | 3/1986 | Tomita et al. | 110/110 |
| 4,579,871 | 4/1986 | Linden et al. | 521/43 |
| 4,588,477 | 5/1986 | Habib | 201/25 |
| 4,726,819 | 2/1988 | Michimae et al. | |
| 4,740,270 | 4/1988 | Roy | 201/35 |
| 4,746,406 | 5/1988 | Timmann | 201/25 |
| 4,787,321 | 11/1988 | Schnelbacher et al. | 110/258 |
| 4,822,573 | 4/1989 | Timmann | 422/143 |
| 4,839,151 | 6/1989 | Apffel | 423/449 |
| 4,851,601 | 7/1989 | Fukuda et al. | 585/241 |
| 4,863,106 | 9/1989 | Perkel | 241/5 |
| 4,871,426 | 10/1989 | Lechert et al. | 201/2.5 |
| 4,895,083 | 1/1990 | McDilda | 110/235 |
| 5,084,141 | 1/1992 | Holland | 201/19 |
| 5,162,446 | 11/1992 | Gibler | 525/338 |
| 5,233,037 | 8/1993 | Nielinger et al. | 540/540 |

OTHER PUBLICATIONS tics (Block, Sheet, Film) After a Controlled Pyrolysis and Crushing," by J. M. Vergnaud et al., pp. 187. 188.

"Pryolysis in a Fluidized Bed-A Recycling Process Developing Towards A Production Scale Plant," H. Timmann.

"Resource Recovery," C95/85, D. V. Jackson et al., 1985 Kirk–Othmer Encyclopedia of Chemical Technology, 3rd Ed., vol. 19, pp. 1002–1010, 1982.

Thermodynamics of Polymerization, H. Swada, Dekker, 1976, pp. 2–5; 7–10; pp. 311–313; 318–325.

Macromolecules, Bovey and Winslow, Academic Press, 1979, pp. 431–433 Encyclopedia of Polymer Science and Engineering, Wiley Interscience, vol. 4, pp. 719–744.

Polymer Handbook, Third Edition, J. Brandrup et al., Wiley Interscience, 1989, pp. II 275–290.

Rubber Chemistry and Technology, vol. 64, "The Ozonation of N,N″-DI-n-Octyl-p-Phenylenediamine and N,N″-DI-(1,1-Dimethylethyl)-p-Phenylenediamine", R. P. Lattimer et al., pp. 780–789.

"Recycling von Altreifen durch Pyrolyse in der Wirbelschicht," Prof. Dr. W. Kaminsky et al., pp. 181–196.

"Pyrolyse von Kunststoffabfällen (Recycling)," Kunststoffe-Plastics, pp. 20–24, Feb. 1986.

"Ein Verfahren zur Abfallbeseitigung und Rohstoffrückgewinung," Dr. Bracker, Herne, pp. 46–48, Apr. 1981.

"Verarbeitung von Kunststoffmüll und Altreifen zu Chemie-Rohstoffen, besonders durch Pyrolyse," Prof. Dr. H. Sinn, et al. pp. 1–35.

Search 1-Report, InfoMaster (R) Service (c) 1990 Telebase4 Systems, Inc., U.S. Patent No. 4,774,655, pp. 29–31, Jun. 6, 1990, Search Parameter: Tires and (Reclaim/or Recycl/) and Depolymer/.

Search 2-Report, Chemical Abstracts (1967-Present) Via Easy Link, pp. 32–60, Jun. 7, 1990 Search Parameter: Tires and (Reclaim/ or Recycl/) and Pyroly/.

U.S. PTO Classification and Search Support Information System (1969 to Date), pp. 1–4, Mar. 23, 1992, (Conducted at Rice University), Search Parameter: Ozon* and (Crack* or Fract* or Fissure or Scission).

U.S. PTO Classification and Search Support Information System, (1969 to Date), Mar. 23, 1992, (Conducted at Rice University), Search Parameter: Ozon* and (Depoly* or Degrad*).

U.S. PTO Classification and Search Support Information System, (1969–Date), pp. 1–21, Mar. 25, 1992, (Conducted at Rice University), Search Parameter: (Plastic or Poly* or Rubber or Tires) and Depoly*.

U.S. PTO Classification and Search Report Information System, (1969–Date), pp. 1–29, Mar. 25, 1992, (Conducted at Rice University), Search Parameter: (Plastic or Poly* or Rubber or Ties) and Ozone*.

U.S. PTO Classification and Search Support Information System (1969–Date), pp. 1–5, Mar. 25, 1992, (Conducted at Rice University), Search Parameter: (Recycl* or Reclam* or Reclaim*) and Ozon*.

DEPOLYMERIZATION METHOD FOR RESOURCE RECOVERY FROM POLYMERIC WASTES

This patent application claims the benefit of and is a continuation-in-part of prior-filed copending U.S. patent application Ser. No. 07/864,426 filed Apr. 6, 1992, now U.S. Pat. No. 5,264,640, entitled "Depolymerization Method for Resource Recovery From Polymeric Matters."

BACKGROUND

1. Field of the Invention

The present invention relates to a depolymerization process for recovering the original monomers from which polymerized products such as scrap or waste tires, rubber and plastics were created. Although reference is made in this application primarily to scrap tires and the recovery of monomers therefrom, it should be understood that a number of different polymerized products can substitute for the scrap tires referenced herein. For example, any polyolefin origin feedstock may be used.

Each year approximately 240 million used tires are discarded. The vast majority of these used tires are put into landfills or, all too often, are disposed of illegally. Such disposal of scrap tires in landfills is becoming increasingly undesirable as significant environmental and social problems are associated with such activity. The availability of landfill space is diminishing, and there has been a national trend toward more stringent regulatory requirements on landfills. Hence, a considerable amount of attention has been devoted recently toward finding alternative uses for and methods of reclaiming scrap tires.

Some research and commercial efforts have been directed toward the development of new uses for old tires. Unprocessed used tires have been used in playgrounds, flower planters, and shoe soles, and tire pieces have been used as gaskets, shims, dock bumpers and shock absorbers. The use of processed used tires in road construction is also gaining some attention. Paving materials made from a combination of crumb rubber and asphalt may last up to three times as long as standard paving materials. However, because of the high costs associated with the use of scrap tires for roads, this approach has not gained wide acceptance. Studies continue to explore this use of scrap tires in addition to the somewhat more conventional use of tires as crash barriers and impact absorbers around highway and bridge abutments. However, these new uses for used tires only consume a minor portion of the annual accumulation of scrap tires.

Consequently, significant research and commercial activity has been directed toward development of the use of scrap tires as an energy source. The 240 million used tires discarded each year represent upwards of $7 \times 10^{13}$ BTU's of energy. Two approaches to tapping this energy source have received most of the attention. In the first, either whole or shredded tires alone are burned for fuel in incinerators or specially designed boilers, in many cases to generate electricity, or are added directly to cement kilns. In many tire incinerators combustion is not complete, resulting in the discharge of smoke and objectionable odors. Meeting federal emissions regulations for any combustion system is costly. In the second approach, tires have the steel belts removed by extensive shredding and are then combined with wood, paper pulp, or other refuse to get a fuel blend that can be burned to provide energy. While the combination of tires with other materials results in a higher total average BTU content for burning as compared to the other materials alone, difficulty in handling, which typically includes special feeding and blending equipment, makes this second approach a rather unattractive method for reclaiming scrap tires. Moreover, for some the incineration of waste plastics has been used to recover their BTU value, identical to the use of scrap tires as fuel.

While such approaches might seem attractive given rising natural-gas and fuel-oil costs, one major drawback to the approach is that valuable basic chemical building blocks or monomers, such as styrene, instead of being recovered, are consumed and are lost forever. The cost of these destroyed or lost monomers includes the costs, in energy and finite natural hydrocarbon resources, of exploration and drilling for new oil and the costs of transporting the crude oil and converting it to the intermediate chemicals from which rubber is made. Ethylene, propylene, butadiene, and styrene are a few examples of olefinic monomers derived from petrochemical sources and used in tire manufacture. The total energy required to make the monomers in the tire is on the order of 60,000 BTU per lb. The fuel energy value of a tire is approximately 15,000 BTU per lb. The cost to the environment of using the valuable monomers as fuel, rather than reclaiming and recycling them, would include the costs of the energy and finite natural resources used to make them, which are permanently lost, versus the relatively meager amount of energy and no natural resources recovered when they consumed. In addition, the costs to the environment of replacing rather than reclaiming the monomers includes the burden of the additional carbon dioxide generated by the energy used in replacement. Carbon dioxide, according to many studies, contributes to global warming. Thus, given the drawbacks associated with these uses for scrap tires, there has been a search for alternative uses for scrap tires that are less costly and that have minimal adverse impact on the environment.

Tires generally consist of rubber, carbon black, steel, fabric and other additives. Styrene-butadiene rubber is most commonly used in tire manufacturing, usually in combination with other elastomers such as natural rubber and ethylene propylene diene monomer (EPDM). Carbon black is used in the manufacture of tires to strengthen the rubber and increase resistance to abrasion. Steel, fiberglass, or fabric in the form of cords or belts is also present for reinforcement in the majority of tires produced today. Finally, other additives, such as antioxidants and antiozonants, are used in the tire manufacturing process to inhibit rubber deterioration and slow aging.

Polymerization is the process in which individual monomers join together in large numbers to form a polymer molecule. Where two different monomers join to form a polymer chain, a copolymer is produced. There are two broad classes of polymers and copolymers based on their polymerization: Condensation polymers, such as polyesters, nylon, polycarbonates, and polyurethanes, are those whose polymerized form has a lower molecular weight than the sum of the monomers used to make it (the balance is generated as other chemicals such as methanol or glycols during polymerization). Addition, or chain-growth, polymers, such as polyethylene and polypropylene, are those whose polymerized form has the same molecular weight as the sum of the monomers used to make them. Addition, or chain-growth, polymers are made in specific conditions of temperature and pressure and in the presence of an initiator (a form of catalyst) in which the polymer chain is propagated, or "zipped" together. Styrene-butadiene rubber, EPDM, and natural rubber, which are the polymers used in tire manufacture, are addition polymers.

There are basically two ways to break down a polymer: pyrolysis and depolymerization. Pyrolysis, also known as thermal cracking, is a process in which polymer molecules are heated until they fragment into several smaller, dissimilar, random-sized molecules. Pyrolysis typically results in the polymer molecules breaking down into a complex mixture of alcohols, hydrocarbons, and other molecules, none of which is an original monomer. Overall, the thermal conditions required for depolymerization are significantly milder than those associated with pyrolysis processes.

Depolymerization, the second way to break down a polymer, is essentially the opposite of polymerization. In the depolymerization of condensation polymers, prior art teaches several hydrolytic methods, such as glycolysis, methanolysis or hydrolysis, categorized by the depolymerization reactant used, such as glycol, methanol or water, respectively, wherein, under specific conditions of temperature and pressure and, sometimes, in the presence of a catalyst, the reactant is added to the polymer causing the polymer chain to separate into its original monomers. An example of these methods is the recycling of PET (polyethylene terephthalate) bottles by a methanolysis process which produces the raw material DMT (dimethyl terephthalate, a precursor to PET), and ethylene glycol. The DMT is then blended with virgin feedstock and FDA-acceptable polymers for food bottles are made. Hydrolytic depolymerization methods have not proven to be effective with addition polymers.

2. The Prior Art

While not limited solely to additive, or chain-growth, polymers, the present invention teaches a method for their depolymerization. The process specifically creates conditions of temperature and pressure and the presence of a catalyst to depropagate or depolymerize these polymers to their constituent monomers. The depolymerization temperature and pressure ranges for many types of polymers and copolymers of the monomers from which the tires are made are well documented in the technical literature. The thermodynamics for the depolymerization of polymers is elucidated in "Thermodynamics of Polymerization" by H. Sawada, published by M. Dekker, 1976. As explained by Sawada, each polymer will have different conditions for depolymerization. For example, polybutadiene depolymerizes in the 325° C. to 475° C. range, while a 75/25 polybutadiene/styrene copolymer depolymerizes in the 327° C. to 430° C. range. Generally, the temperatures involved in the depolymerization of the polymers and copolymers from which tires are made are in the 135° C. to 500° C. range. However, neither the technical literature nor prior patents teach a process for the depolymerization of addition polymers on a commercial basis.

The stress cracking of rubber by ozone has been known for decades. Ball and Youmans reported in Rubber Age 55, 481-3, 1944, that sheets of carbon black vulcanizates of tire tread cracked in 30 minutes in ozonized air at temperatures of 25° F., thus demonstrating that treatment with ozone gas will cause cleavage of vulcanized rubber molecular linkages. Baker and King in 1950 and Allison and Stanley in 1952 reported that stressed natural and synthetic rubbers relax when exposed to ozonized air. The inclusion of antioxidants and antiozonate chemicals in rubbers and polymers has been and is being practiced to suppress the deleterious effects of ozone and is well documented in prior art. The present invention teaches the use of ozone treatment to break down the cross-linked rubber making it more susceptible to thermal depolymerization thus using an otherwise 'undesirable' reaction to its advantage. While the deleterious effect of ozone on rubber and other polymers has been known for a considerable time, there is no readily available information that past investigators utilized ozone to beneficially enhance a depolymerization reaction process.

SUMMARY OF THE INVENTION

The principal objective of this invention is to provide an environmentally acceptable and economically feasible process whereby the hydrocarbon feedstocks, or monomers, from which polymers are made can be recovered for reuse.

A further objective is to apply depolymerization technology to cause the polymer molecule to break down into the molecules from which it was made.

An additional objective is to simplify and improve the process and the final product recovery by the addition of a feedstock washing step for removing interfering complex chemical additives from the feedstock and by improving the fracturing of the chemical bonds within the polymer by exposure to ozone gas.

An additional objective of this invention is to overcome problems of scaling and to satisfy production capacity requirements by employing up to two or more moderately sized depolymerization reactors operating simultaneously under similar process conditions.

Another objective of this invention is to provide a process whereby the reclamation of waste polymers does not contribute pollutants to the atmosphere as does the burning of tires to produce energy. Along with that objective, it is an objective to recover and preserve monomers and other chemicals for reuse instead of destroying them as does the burning of tires to produce energy.

Another objective of this invention is to provide a process which will provide reuseable monomers at a cost lower than the cost of manufacturing fresh monomer feedstocks from crude oil or natural gas.

These and other objectives of this invention are accomplished, in broad aspect, by the thermocatalytic depolymerization of finely divided polymers in the presence of combinations of metallic salt catalysts.

The method of the present invention generally may be considered in three sections: (1) the feed preparation section; (2) the reaction section; and (3) the product recovery section. The method begins with the acquisition of finely divided particles of used tire rubber having a particle size range of about −6 to +25 mesh. Finely divided particles are used to: (1) maximize the surface area available for the depolymerization reaction; (2) minimize the residence time in the depolymerization reactor, thereby decreasing the opportunity for pyrolysis of the rubber and/or the further degradation of the depolymerized volatile matter; and (3) to provide the maximum surface area of the rubber for the ozone stress cracking treatment. The desired particle size of the finely divided rubber particulate is dictated in part by the very poor thermal conductivity of the rubber. Further, as the depolymerization reaction proceeds, the individual particles continuously diminish in size, exposing fresh surfaces for further reaction. Thus, the smaller the initial size of the particles, the lower the capital cost of the reaction system.

It is known that tire manufacturers compound into rubber a number of additives and fillers, each having its own function in the performance and life of the tire. Antioxidants and antiozonates, for example, are chemicals compounded into the rubber by tire manufacturers to protect the tire from stress cracking attack by oxygen and ozone. The technical paper, "The Ozonation of N,N'-Di-n-Octyl-p-Phenylene-diamine and N,N'-Di-(1,1'-Dimethylethyl)-p-Phenylenediamine", authored by Messrs. Latimer, Layer, Hooser and Rhee of B. F. Goodrich in 1991, discloses that the ozonation of these complex chemicals also produces even more complex chemicals. In addition, it is known that such incorporated additives and fillers in plastics and rubber gradually "bloom" to the surface of the rubber where they carry out their desired function. Thus, an additional advantage of starting with finely divided rubber particles is that the distance through which the additives and fillers must migrate is short, so that by the time the rubber particles are introduced into the process the additives have "bloomed" to the surface.

The complex chemical additives typically introduced into rubber are soluble in common organic solvents such as alcohols, ethers, tetrahydrofuran and the like. In the present invention, once the additives have "bloomed" to the surface of the rubber particles the additives are removed from the particulate by washing with any of several organic solvents. Thus, contamination of the final product stream by the additives is avoided, and the recovery of the desired monomeric products is simplified. Also, removed additives and other oils in the formulation have a monetary value and can be recovered from the solvent by common separation techniques. Fillers such as carbon black are also present in the rubber particle. These fillers typically are inorganic chemicals added to the rubber during the post-polymerization compounding step to enhance the properties of the rubber. However, these fillers generally will remain embedded within the rubber particles after the washing.

Thus, the first step in the process of the present invention involves washing the finely divided particles to remove additives present on the surface of the particles. The washing step generally, consists of rinsing the rubber particulate with an appropriate solvent. The particulate is slurried in the solvent, the contaminated solvent is drained off, and the particulate is air dried. Typically, the solvent may be used for several rinsings before it becomes saturated with the additives and needs to be reclaimed. If contaminated solvent is used for the rinsing, a second rinsing with a purer solvent may be desired to remove traces of the additives from the surface of the particulate.

After the rubber particulate is rinsed and dried, the finely divided particles are mechanically conveyed into one of the ozone treatment and storage silos where exposure of the rubber to gaseous ozone causes stress cracking on the surface of the rubber particles, and rupturing of the crosslinked chemical bonds, making the rubber much more susceptible to subsequent thermal and thermocatalytic depolymerization. The ozone treatment thus provides a desirable reaction instead of its normally undesirable reaction with rubber products. Although the concentration of ozone gas in air in the ozone treatment silos typically is maintained at a concentration of about 3 parts per thousand, the concentration may vary depending on the demands of the process.

The reaction section starts with the transfer of the rubber particulate to the reaction feed silo. The transfer of the rubber particulate is done generally by mechanical means, such as augers, since the finely divided rubber particles have a high coefficient of friction and very poor flow characteristics. The reaction section operates at a partial vacuum to facilitate the rapid removal of the monomers as they are separated from the rubber polymer. The flow of rubber from the reaction section feed silo to the individual depolymerization reactors is on a continuous basis. A series of smaller individual reactors typically is used instead of a single larger depolymerization reactor, with the reactors having the same or similar designs and operating at the same or similar process conditions.

The reaction section is maintained at a vacuum of approximately 27 inches of mercury. The influence of reduced pressure on the temperature for depolymerization is shown, for example, by the tact that the depolymerization of polystyrene requires a temperature of 235° C. at atmospheric pressure and a temperature of 200° C. at 10 Torr pressure. The overall operating temperatures of the individual reactors are typically in the 300° C. to 550° C. range, although temperatures as low as the ceiling temperature for a particular composition or as high as 600° C. or more are contemplated. Again, operating temperature is pressure dependent. The temperature within the reactor may be fixed, or it may be cycled between upper and lower temperature limits depending on the particular application.

The reactors are heated by heat transfer fluids, with final temperature adjustment provided by electrical resistance heaters. Because of the possible evolution of corrosive gases, the inside of the reactor typically is clad with an appropriate alloy steel. The reactor is a vertical, cylindrically shaped, stirred vessel fitted with appropriate top mounted ports to receive the particulate feed and discharge the separated monomer gases.

Regarding the depolymerization reaction, it is well known that competing reactions occur in polymerization chemistry. The predominating reaction rate is a function of the temperature. The higher the temperature the greater the rate of decomposition or depolymerization reactions. Also, per Sawada, there is a ceiling temperature above which the depolymerization reaction rate predominates. The ceiling temperature is different for each monomer type. The ceiling temperatures of monomers of interest range from about 200° C. to about 550° C. Thus, the preferred reaction temperature is not a fixed temperature but is the temperature required for the specific rubber polymers involved. Generally, though, the more complex the molecule or the higher its molecular weight, the higher its ceiling temperature.

Conditions do exist wherein the depolymerization reaction overwhelms the polymerization reaction, and generally catalyst systems are involved. Basically, the rubbers and polymers to be treated have been polymerized by combinations of catalysts, organometallic halides, metallic salts, metallic oxides, free radical initiators and the like. A combination of catalyst technologies are involved. In these combinations, magnesium dichloride or triethyl aluminum (TEAL) are usually involved as a cocatalyst. Referring to the Periodic Chart of the Elements, it is noted that the base metal in the majority of high activity addition polymerization metallic salt catalysts are in classes III, IVB, and VIB having an electron structure that satisfies the acceptor/donor exchange requirement with the polymer undergoing decomposition or depolymerization. From the above, and other findings, it has been deduced that a molten $MgCl_2/AlCl_3$ catalyst combination will thermocatalytically cause the thermal depolymerization degradation of polymers and rubber in the temperature range described above. Other catalysts or catalyst systems which may be used include: $BaCl_2/AlCl_3$; $LiAlCl_4$; $NaAlCl_4$; $KAlCl_4$; and other combinations of two non-transition metal halides. The ratio of $MgCl_2$ to $AlCl_3$ is maintained to maximize the depolymerization of the polymer or rubber being processed. Generally, this ratio will be in the range of about 1:1 to about 2:1 on a molar basis. As the depolymerization reaction proceeds there will be a slow depletion of the $MgCl_2/AlCl_3$ catalyst on a ratio of about 1:50,000 of rubber processed. Make-up catalyst thus will need to be added to the reactor periodically to sustain the reaction.

The separated monomers exit the reactor as gases, passing through treatment beds to neutralize any HCl generated and to absorb any $H_2S$ similarly evolved. Subsequently, the monomeric gases are condensed as a mixture in the product condensate recovery tank. From this point the condensed gases are pumped to the product recovery section where the components of the mixture are separated by essentially conventional distillation techniques.

Examples of the more important features of this invention have been broadly outlined in order that the detailed description that follows may be better understood and so that contributions which this invention provides to the art may be better appreciated. There are, of course, additional features of the invention which will be described herein and which will be included within the subject matter of the claims appended hereto.

DETAILED DESCRIPTION OF THE INVENTION

Figure 1:
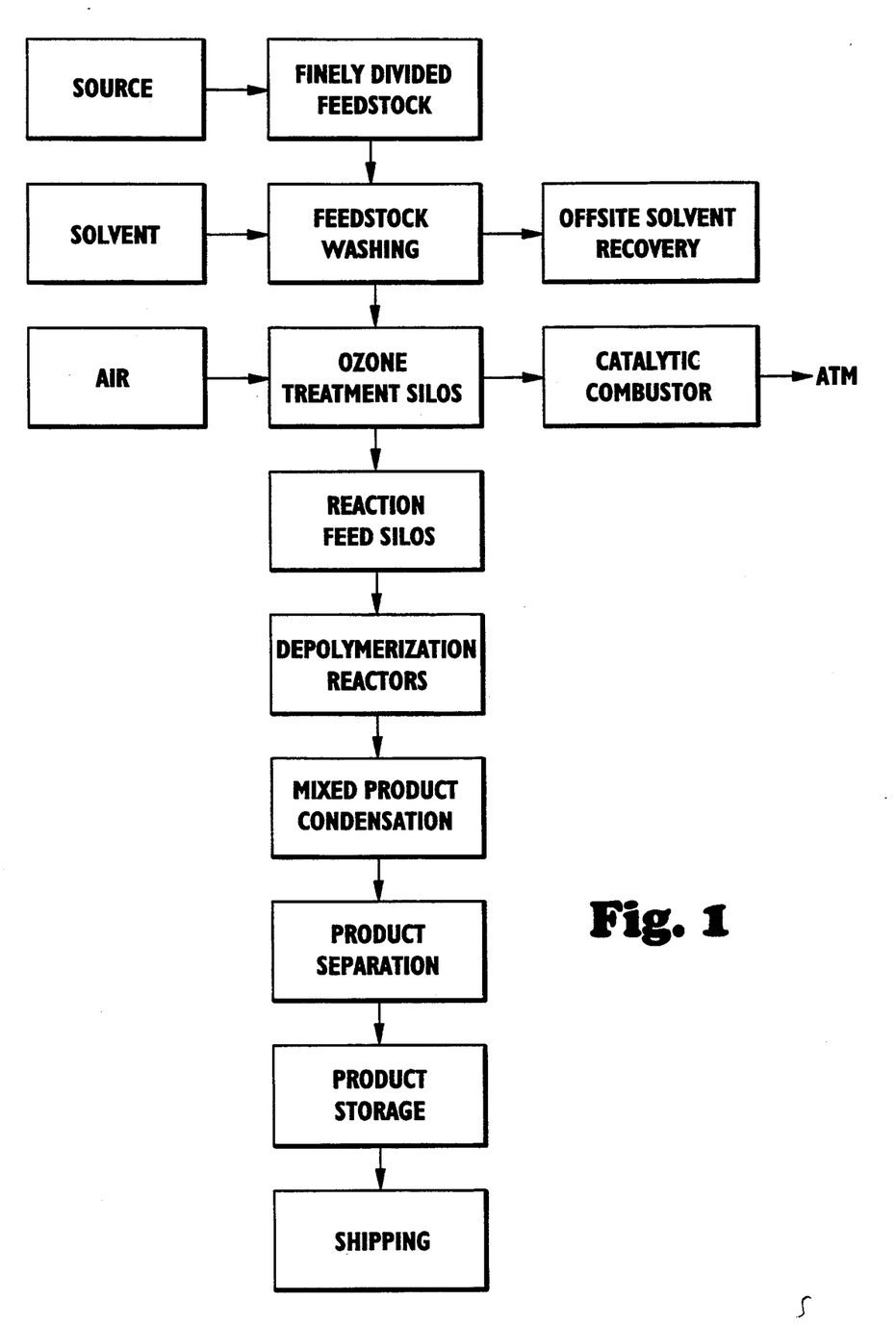
FIG. 1 is a block flow diagram of the process of this invention.

Additional objects, features and advantages of the present invention will become apparent by referring to the following description of the invention in connection with the accompanying drawings. The basic processes for the depolymerization of used tire rubber and waste plastics are for the most part identical. Thus, although waste plastics can be depolymerized according to the present invention, for simplicity reference is only made to the processing of used tire rubber. A block flow diagram of the process of this invention is shown in FIG. 1. As indicated therein, a prelude to the depolymerization of used tires will be the collection of used tires, the shredding of the rubber into a small specified size, and the separation of the steel wire and fabric from the rubber particles.

Feed Preparation Section

Figure 2:
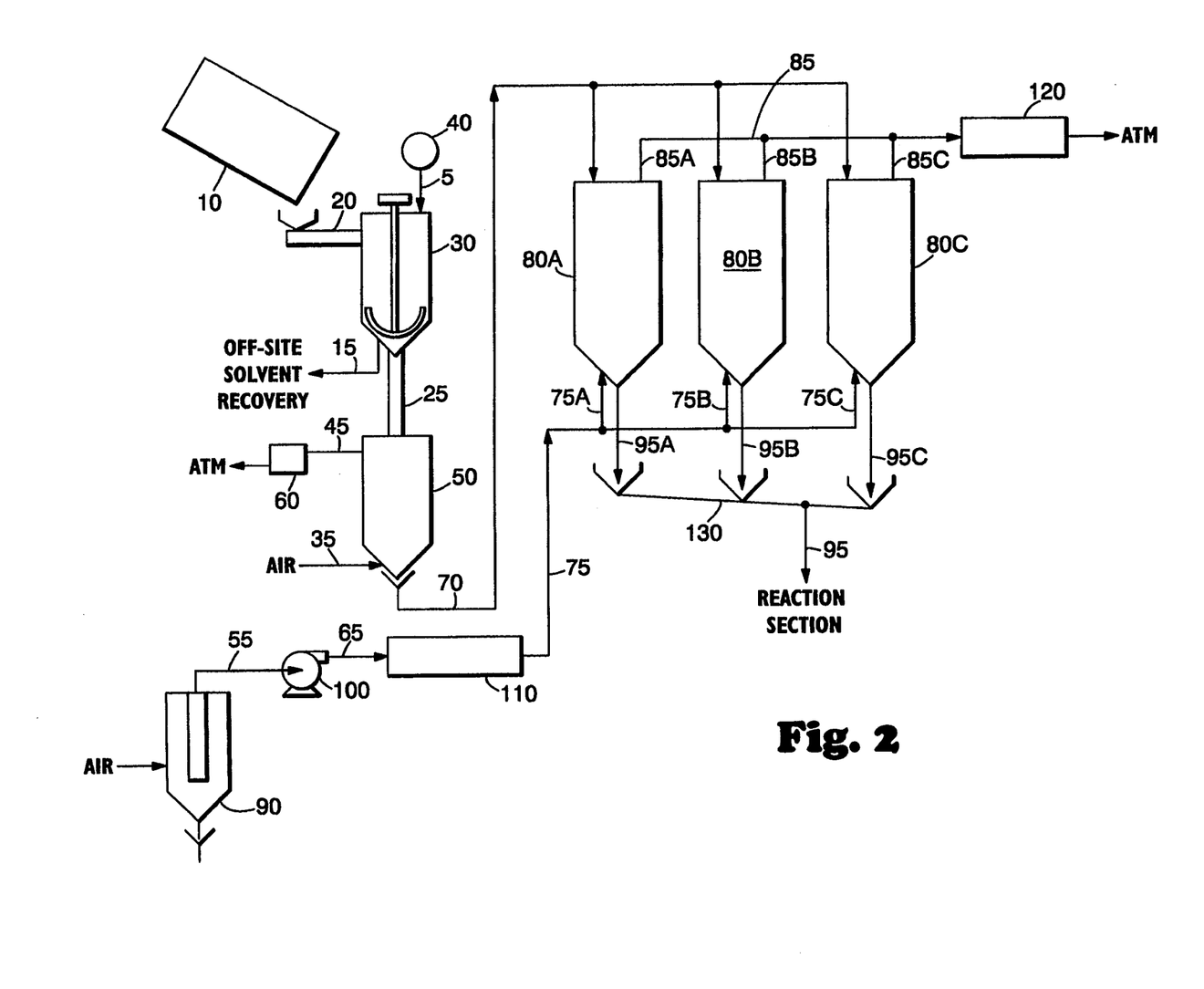
FIG. 2 is a schematic representation of the feed preparation section of the process of this invention.

As illustrated in FIG. 2, finely divided used tire rubber particles of about −6 to +25 mesh are received from off-site sources via a hopper car or truck 10. These particles are mechanically conveyed into wash tank 30 via feed auger 20. The finely divided particulate, which is coated with additives and probably also with dirt and dust, is washed with a solvent fed via line 5 from solvent storage tank 40 into wash tank 30. The particulate as a slurry is washed in batches by the solvent. Contaminated solvent containing removed additives and other contaminants such as dust and dirt is drained from wash tank 30 through line 15 to an off-site location for reclamation of the solvent for recycle, with the removed and recovered chemical additives being processed later off-site for reuse.

The washed particulate is transferred from the wash tank 30 to drier vessel 50 by auger or other suitable mechanical means through line 25. Vessel 50 is flushed with air entering vessel 50 through line 35. The volume of air flushed through vessel 50 is sufficient to ensure that no hazard of gaseous explosion can occur. The air exits vessel 50 via line 45 enroute to catalytic combustor 60 where traces of hydrocarbons are converted to non-polluting carbon dioxide and water which is discharged safely to the atmosphere.

The washed and dried particulate is discharged directly into mechanical conveyor 70 which conveys the particulate and discharges it into one or more ozone treatment silos 80A, 80B and 80C. In the treatment silos, the particulate is exposed to a 0.01 weight per cent concentration of gaseous ozone in air. During the residence of the particulate in the silos the ozone gas causes the cross-linked chemical bonds of the rubber to rupture, thus facilitating a higher conversion of rubber polymer to monomers later in the process.

Air is filtered in bag filter 90 and passed via line 55 to blower 100. Ozone gas in air is generated from the filtered air in the ozone generator 110. The ozonized air is pumped via line 75 into and through silos 80A, 80B and 80C by the pressure provided by centrifugal blower 100. Blower 100 typically will maintain a pressure of about 3 to 5 psig in the downstream ozone generator 110 and ozone treatment silos 80A, 80B and 80C. The pressurized air flows from blower 100 via line 65 to ozone generator 110 which converts some of the oxygen in the air to ozone in a concentration preferably of about 0.01 weight percent ozone in air. The ozonized air mixture passes upward through the ozone treatment silos via lines 75A, 75B, and 75C exiting the top of the silos through lines 85A, 85B, and 85C enroute via line 85 to the catalytic ozone decomposer 120. The decomposed ozonized air will be discharged to the atmosphere as non-polluting. Flow through the silos is terminated intermittently with the ozone gas in the silos "locked in" to continue attack on the chemical bonds of the particulate. Upon demand the particulate is discharged from the silos through lines 95A, 95B, and 95C and conveyed by mechanical conveyor 130 through line 95 to the depolymerization reaction section.

Depolymerization Reaction Section

Figure 3:
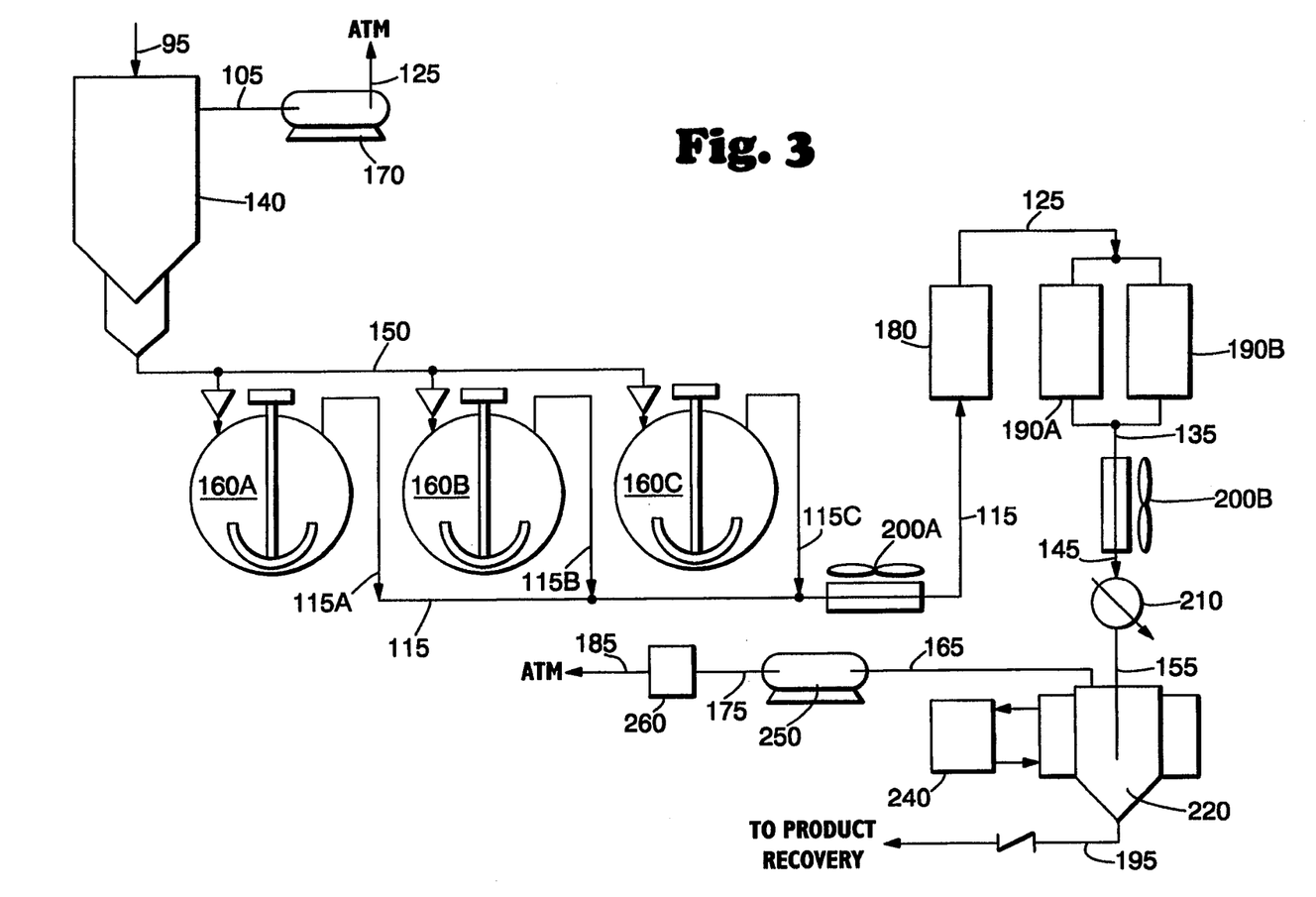
FIG. 3 is a schematic representation of the depolymerization reaction section of the process of this invention.

The particulate is conveyed by mechanical means through line 95 and is discharged into reaction feed silo 140. Reaction feed silo 140 is maintained at a partial vacuum about equal to that of depolymerization reactors 160A, 160B and 160C by vacuum pump 170 through line 105. The vacuum pump discharge through line 125 joins line 85 and exits through the ozone catalytic converter 120 to the atmosphere. The particulate is mechanically conveyed via conveyor 150 and discharged either continuously or intermittently into stirred depolymerization reactors 160A, 160B and 160C through top mounted hoppers. The depolymerization reactors 160A, 160B and 160C are heated externally and maintained at the desired reaction temperature by heat transfer fluids passing through externally mounted panel coils which typically are part of the Pfaudler type alloy lined stirred reactors. A blend of metallic halide catalysts is added periodically to depolymerization reactors 160A, 160B and 160C through the top mounted hoppers to replace catalyst depleted by the depolymerization reaction.

Depolymerized monomers formed as gases exit the top of the Pfaudler type reactors 160A, 160B and 160C through lines 115A, 115B and 115C, respectively, to line 115. The hot monomeric stream 115 is cooled by air cooled heat exchanger 200A. The stream 115 then passes upward through a neutralizing caustic bed 180 to neutralize any HCl vapors formed during the depolymerization reactions.

The heat of adsorption of the molecular sieve beds 190A and 190B increases the heat of the monomeric gases exiting via line 135. The product gases thus are cooled in a second air cooled heat exchanger 200B before passing via line 145 to chilled water heat exchanger 210 where further cooling occurs. The monomeric gases, under a partial vacuum provided by vacuum pump 250, exit via line 155 and are condensed in the jacketed refrigerated mixed product condensate tank 220. A refrigeration unit 240 provides the refrigeration for the mixed product condensate tank 220.

Mixed liquid product collected in tank 220 is moved via line 195 to the vacuum short path distillation product recovery section or equivalent, where the individual liquified monomers are separated and purified before storage and shipping. Any vapors removed from the mixed liquid product condensate tank 220 are discharged via line 165 by vacuum pump 250 and pass through line 175 to catalytic combustor 260 to ensure that atmospheric emissions of hydrocarbons are avoided. The discharge from combustor 260 passes to the atmosphere via line 185. The temperature of the mixed product condensate is tank 220 typically is maintained well below the reduced pressure boiling point of the recovered monomers, generally through the use of non-chlorinated fluorocarbon refrigerants, such as propane or ammonia.

Although the preferred embodiment of this invention has been described hereinabove in some detail, it should be appreciated that a variety of embodiments will be readily available to persons utilizing such depolymerization resource recovery methods for a specific end use. The description of the method of this invention is not intended to be limiting on this invention, but is merely illustrative of the preferred embodiment of this invention. Other methods of resource recovery which incorporate modifications or changes to that which has been described herein are equally included within this application.

What is claimed is:

1. A process for recovering a monomer from a vulcanized addition polymer feedstock formed at least from the monomer and from compounded additives, comprising the steps of:
   (a) washing the addition polymer feedstock to remove the additives from the surface of the feedstock;
   (b) exposing the washed feedstock to gaseous ozone under conditions sufficient to rupture chemical bonds formed during the vulcanization process of the addition polymer feedstock and thereby form one or more intermediate products;
   (c) heating in the presence of a catalyst the mixture formed in step (b) to a temperature and for a time sufficient to depolymerize the addition polymer and form the monomer; and
   (d) removing the monomer following its formation from the mixture.

2. The process of claim 1 wherein the washed addition polymer feedstock is exposed to a mixture of gaseous ozone and air.

3. The process of claim 2 wherein the mixture of gaseous ozone and air comprises about 0.01 percent by weight of gaseous ozone.

4. The process of claim 1 wherein the addition polymer feedstock is exposed to gaseous ozone under conditions to rupture cross-linked bonds of the addition polymer feedstock.

5. The process of claim 1 wherein the addition polymer feedstock comprises particles ranging in size from about −6 to +25 mesh.

6. The process of claim 1 wherein the reaction of step (c) is carded out at a temperature of between about 200° C. and about 600° C.

7. The process of claim 1 wherein the reaction temperature of step (c) is cycled between about 300° C. and 550° C.

8. The process of claim 1 wherein the depolymerization reaction takes place in the presence of a thermocatalytic catalyst.

9. The process of claim 1 wherein the depolymerization reaction takes place in the presence of thermocatalytic catalyst system which is a combination of metallic halides.

10. The process of claim 9 wherein the thermocatalytic catalyst system is a combination of magnesium dichloride and aluminum trichloride.

11. The process of claim 10 wherein the molar ratio of the magnesium dichloride and aluminum trichloride is between about 1:1 and about 2:1.

12. The process of claim 1 wherein the reaction of step (c) is carried out at a pressure from about 0.05 to about 0.25 atmospheres.

13. The process of claim 1 wherein the addition polymer feedstock is rubber reclaimed from used tires.

14. The process of claim 1 wherein the addition polymer feedstock is of polyolefin origin.

15. The process of claim 1 wherein the addition polymer feedstock is made up of a blend of addition copolymer feedstocks.

* * * * *

UNITED STATES PATENT AND TRADEMARK OFFICE
CERTIFICATE OF CORRECTION

PATENT NO. : 5,369,215
DATED : November 29, 1994
INVENTOR(S) : Gerald A. Platz

It is certified that error appears in the above-indentified patent and that said Letters Patent is hereby corrected as shown below:

On title page, item [75] "Gerald A. Platz" should read ---Gerald M. Platz---
Column 10, line 36, "carded" should read carried---

Signed and Sealed this

Twenty-fifth Day of April, 1995

Attest:

BRUCE LEHMAN

*Attesting Officer*  *Commissioner of Patents and Trademarks*